(12) United States Patent
Baba et al.

(10) Patent No.: US 6,895,080 B2
(45) Date of Patent: May 17, 2005

(54) X-RAY MEASURING APPARATUS

(75) Inventors: Rika Baba, Kodaira (JP); Ken Ueda, Ome (JP)

(73) Assignee: Hitachi Medical Corporation, Tokyo (JP)

( * ) Notice: Subject to any disclaimer, the term of this patent is extended or adjusted under 35 U.S.C. 154(b) by 139 days.

(21) Appl. No.: 10/296,511

(22) PCT Filed: Jun. 12, 2001

(86) PCT No.: PCT/JP01/04946

§ 371 (c)(1),
(2), (4) Date: Nov. 26, 2002

(87) PCT Pub. No.: WO02/04932

PCT Pub. Date: Jan. 17, 2002

(65) Prior Publication Data

US 2004/0013224 A1 Jan. 22, 2004

(30) Foreign Application Priority Data

Jul. 10, 2000 (JP) ...................................... 2000-213370

(51) Int. Cl.$^7$ ................................................ G21K 1/00
(52) U.S. Cl. ........................ 378/154; 378/155; 378/147; 378/98.8
(58) Field of Search ................................ 378/154, 155, 378/147, 98.8, 19; 250/370.09

(56) References Cited

U.S. PATENT DOCUMENTS

| | | | | |
|---|---|---|---|---|
| 5,949,850 A | * | 9/1999 | Tang ........................... | 378/154 |
| 6,167,115 A | * | 12/2000 | Inoue .......................... | 378/155 |
| 6,177,237 B1 | * | 1/2001 | Guida et al. ................. | 430/320 |
| 6,282,264 B1 | * | 8/2001 | Smith et al. ................. | 378/189 |

FOREIGN PATENT DOCUMENTS

| | | |
|---|---|---|
| JP | 09197051 | 5/1928 |
| JP | 04308809 | 10/1992 |
| JP | 0975332 | 3/1997 |
| JP | 09066054 | 3/1997 |
| JP | 09149895 | 6/1997 |
| JP | 10192267 | 7/1998 |
| JP | 11226004 | 8/1999 |

OTHER PUBLICATIONS

Image Engineering: Shin Hasegasa, Corona Publishing Co., Ltd., pp 195–199.
Journal of Optical Society of America, vol. 1(6) pp. 612–619, 1984 "Practical Cone–Beam Algorithm".
Trend of Flat Panel Detector: Kiyonari Inamura, Video Information, vol. 31(4) pp 125–130.

* cited by examiner

Primary Examiner—Craig E. Church
Assistant Examiner—Irakli Kiknadze
(74) Attorney, Agent, or Firm—Antonelli, Terry, Stout & Kraus, LLP

(57) ABSTRACT

The present invention provides an x-ray measuring apparatus for diagnosis having high spatial resolution and high sensitivity, which includes: an x-ray source for emitting x-rays from an x-ray focal spot; an x-ray detector in which a plurality of sensing elements each having a sensitive part and a blind part surrounding the sensitive part are arranged two-dimensionally; data processing means for collecting output signals of the sensing elements and performing data processing; and an anti-scatter grid disposed between the x-ray focal spot and the x-ray detector with predetermined distance from the position of the x-ray focal spot and in which an x-ray transmitting member and an x-ray shielding member are alternately arranged in a first direction. A pitch in the first direction of linear images projected on a sensing surface of the x-ray detector of the x-ray shielding member by the x-ray is set to be substantially an integral multiple of two or larger of the pitch of arrangement of the sensing elements in the first direction. In such a manner, a moiré-free image of a wide field of view is obtained.

10 Claims, 6 Drawing Sheets

X-RAY MEASURING APPARATUS

TECHNICAL FIELD

The present invention relates to x-ray measuring apparatuses such as an x-ray image acquiring apparatus, an x-ray fluoroscopic apparatus, and a cone-beam computed tomographic (CT) apparatus capable of acquiring an image of a high picture quality by using a flat-type x-ray detector.

BACKGROUND ART

An x-ray fluoroscopic apparatus and an x-ray image acquiring apparatus for measuring an x-ray image by using a two-dimensional x-ray detector are known techniques. There are a cone-beam CT for performing image acquisition while rotating an x-ray source and a two-dimensional x-ray detector around the subject, and a cone-beam CT for performing image acquisition while fixing an x-ray source and a two-dimensional x-ray detector and rotating the subject (Japanese Patent Application Laid-Open No. 10-192267: prior art 1).

In the cone-beam CT, by performing a correcting process on each of a plurality of images acquired by the rotation image acquisition, a set of projection data is obtained. By performing a three-dimensional reconstructing process by using a three-dimensional reconstruction algorithm on the set of projection data acquired, a three-dimensional image is obtained.

The three-dimensional reconstruction algorithm of CT is described in "Image Engineering" (by Shin Hasegawa, Corona Publishing Co., Ltd., pp. 195–199: prior art 2). As the three-dimensional reconstruction algorithm of cone-beam CT, a method such as Feldkamp method is used. Particularly, the Feldkamp method is described in "Practical cone beam algorithm" (L. A. Feldkamp, Journal of Optical Society of America, Vol. 1(6), pp. 612–619, 1984: prior art 3).

Two-dimensional x-ray detectors used for cone-beam CT include an XII-camera type x-ray detector obtained by combining an x-ray image intensifier (hereinbelow, abbreviated as XII) and a TV camera via an optical system (Japanese Patent Application Laid-Open No. 10-192267: prior art 1), and a flat-type x-ray detector.

The flat-type x-ray detector and the possibility of applying the detector to tomography is described in "Trend of Flat Panel Detector" (Kiyonari Inamura, Video Information, vol. 31(4), pp 125–130: prior art 4).

For example, the configuration of a plat-type x-ray detector in which sets each of an amorphous silicon diode (hereinbelow, abbreviated as a-SiPD) and a TFT are arranged in a square matrix and the sets and a fluorescent screen are directly combined is known. In a flat-panel type x-ray detector of this type, an x-ray is incident on the fluorescent screen, thereby generating fluorescence which enters the nearest a-SiPD and is converted into charges. The charges are accumulated until being read. In this example, the a-SiPD functions as a discrete sensing element.

An example of means for reducing scattering x-rays which are incident on the two-dimensional x-ray detector is a scattering x-ray shielding grid (hereinbelow, simply called anti-scatter grid). By disposing the anti-scatter grid on the front face of the two-dimensional x-ray detector, scattering rays can be reduced in x-ray fluoroscopy, x-ray image acquisition, and cone-beam CT image acquisition.

The anti-scatter grid has a stacked structure in which an x-ray transmitting member such as aluminum and an x-ray shielding material such as lead are alternately stacked. There is a cross anti-scatter grid in which two anti-scatter grids each having the stack structure are disposed so as to perpendicularly cross each other and integrated. It is known that an anti-scatter grid for blocking scattering x-rays for cone-beam CT image acquisition (Japanese Patent Application Laid-Open No. 9-149895: prior art 5).

A technique of binning which adds output signals of a plurality of sensing elements of a two-dimensional x-ray detector in a one-dimensional direction or two-dimensional direction is known (Japanese Patent Application Laid-Open No. 9-197051: prior art 6). It is known that, in an XII-camera type x-ray detector, the number of output pixels of a TV camera can be changed. The technique is known also in cone-beam CT image acquisition (Japanese Patent Application Laid-Open No. 11-226004: prior art 7).

The binning can realize an effect of decreasing the number of data of output signals and reducing time for outputting an image and an effect of shortening time required for data processing. After temporarily storing output signals of sensing elements into a memory, binning may be performed in a post process, thereby enabling time required for a computing process after the binning to be shortened.

Another known technique is that the pitch of x-ray shielding members of an anti-scatter grid projected on the surface of sensing elements of the flat-type x-ray detector with x-rays is set to a fraction of an integer of the arrangement pitch of sensing elements (Japanese Patent Application Laid-Open No. 9-75332: prior art 8).

There is also a known method of matching the position of an x-ray source and the position of an anti-scatter grid by using the shadow of an x-ray shielding member of an anti-scatter grid projected on the surface of sensing elements of a flat-type x-ray detector with x-rays (Japanese Patent Application Laid-Open No. 4-308809: prior art 9).

There is also a known method of aligning an x-ray source and a detector by using the shadow of an x-ray shielding member of an anti-scatter grid projected on the surface of sensing elements of a flat-type x-ray detector with x-rays (Japanese Patent Application Laid-Open No. 9-66054: prior art 10).

First, terms used for the following description will be explained.

(1) amorphous silicon photo diode: In the following description, it will be abbreviated as a-SiPD.

(2) scattering x-ray shielding grid: In the following description, it will be simply called an anti-scatter grid.

(3) flat-type x-ray detector: an x-ray detector in which sensing elements are arranged in a two-dimensional plane. In the following description, it will be simply called an x-ray detector.

(4) sensing element: In an example to be described below, a sensing element is constructed by a set of an a-SiPD and a TFT and a fluorescent layer. The sensing element includes a sensitive part in which an a-SiPD for changing fluorescence generated by the fluorescent layer with an x-ray into an electric signal is formed and a blind part which is the part other than the sensitive part.

(5) sensing surface: In an example to be described below, a sensing surface is a surface on which a plurality of a-SiPDs are formed in a flat-type x-ray detector.

In an x-ray measuring apparatus for diagnosis such as an x-ray fluoroscopic apparatus, an x-ray image acquiring apparatus, and a cone-beam CT apparatus for measuring an x-ray image by using an x-ray detector, improvement in a spatial resolution is required to improve diagnostic performance, so that the size of the sensing elements of the x-ray detector is being reduced. In the x-ray measuring apparatus for diagnosis, in addition to improvement in spatial resolution, reduction in an x-ray exposure amount is also required, so that higher sensitivity of x-ray detection is demanded.

In the case of using an x-ray detector, there is a problem such that deterioration in picture quality by scattering x-rays cannot be avoided. In the case of adjusting the pitch of x-ray shielding members of the anti-scatter grid to the pitch of sensing elements in order to reduce scattering x-rays, as the size of the sensing elements is reduced, the pitch of the x-ray shielding members becomes smaller. It causes deterioration in sensitivity by the anti-scatter grid and a problem arises such that exposure of x-rays has to be increased to obtain predetermined sensitivity. It can be considered that, when the size of the sensing element is reduced, the pitch of x-ray shielding members in the anti-scatter grid is set in correspondence with the pitch of a plurality of sensing element groups, thereby setting the pitch of the x-ray shielding members to be larger than that of sensing elements.

However, any of the above cases has a problem such that moiré occurs due to loss of the corresponding relation between the arrangement pitch of x-ray shielding members and the pitch in the sensing distribution of the x-ray detector. Particularly, since a sensing distribution characteristic is sharp in the x-ray detector, moiré tends to occur. In a cone-beam CT image, there is a problem such that degradation occurs in picture quality due to artifact caused by moiré and quantitativeness of a CT value deteriorates. For example, the inventor herein has found, as shown in FIG. 6, not only a ring artifact but also an artifact which has a plurality of curved parts derived from a ring and is generally very complicated. FIG. 6 shows an example of the artifact which appears in the center portion of a reconstructed image of a water phantom of a cylindrical shape having a large diameter.

In an x-ray measuring apparatus using an x-ray detector having small-sized sensing elements, it is desired to effectively reduce scattering x-rays and realize higher sensitivity and higher spatial resolution without deteriorating sensitivity.

DISCLOSURE OF THE INVENTION

An object of the present invention is to provide an x-ray measuring apparatus for diagnosis capable of obtaining a moiré-free image of a large field of view with high spatial resolution and high sensitivity.

An x-ray measuring apparatus to which the invention is applied includes: an x-ray source for emitting x-rays from an x-ray focal spot to a subject; an x-ray detector in which a plurality of sensing elements each having a sensitive part and a blind part surrounding the sensitive part are arranged two-dimensionally; data processing means for collecting output signals of the plurality of sensing elements by performing image acquisition control and for performing data processing; and an anti-scatter grid for blocking scattering rays, which is disposed between the x-ray focal spot and the flat-type x-ray detector, with predetermined distance from the position of the x-ray focal spot, in which an x-ray transmitting member and an x-ray shielding member are alternately arranged in a first direction, and which is fixed by a thin x-ray transmission plate.

For example, the x-ray detector has a known configuration in which a plurality of sets each having an a-SiPD independently functioning via a blind part and a TFT are arranged in a square matrix and a fluorescent layer (plate) are directly combined with each other. A sensing element is constructed by the set of an a-SiPD and a TFT and the fluorescent layer. An x-ray passed through the subject passes through the anti-scatter grid and is incident on the fluorescent layer. Fluorescence generated by the fluorescent layer is incident on the closest a-SiPD and converted to charges which are stored until being read.

In a state where the subject is not disposed, a linear projection image of the x-ray shielding members of the anti-scatter grid can be obtained on the sensing surface (surface where a plurality of a-SiPDs are formed) of the x-ray detector by irradiation of x-rays.

In a first configuration of the invention, the pitch in one direction of linear images of the x-ray shielding members of the anti-scatter grid projected on a sensing surface of the x-ray detector is set to be substantially an integral multiple of two or larger of the pitch of arrangement of the sensing elements in the one direction. With the configuration, a moiré-free image of a large field of view can be obtained with high spatial resolution and high sensitivity.

In the first configuration, the data processing means performs a process of adding output signals of the plurality of sensing elements which are adjacent to each other. By binning output signals of the plurality of sensing elements, a moiré-free image can be obtained with high spatial resolution and high sensitivity at high speed.

In the first configuration, the anti-scatter grid is disposed between the x-ray focal spot and the x-ray detector with a predetermined fixed distance from the position of the x-ray focal spot, and the x-ray measuring apparatus further includes adjusting means for adjusting the interval between the position of a surface formed by end portions on the x-ray incident surface side of the plurality of x-ray shielding members of the anti-scatter grid and the position of a sensing surface (surface on which a plurality of a-SiPDs are formed) of the x-ray detector in a direction connecting the x-ray focal spot and the center portion of the anti-scatter grid. The adjusting means can adjust the interval in a state where the surface formed by end portions on the x-ray incident surface side of the plurality of x-ray shielding members of the anti-scatter grid and the sensing surface of the x-ray detector is held substantially parallel to each other.

Since the configuration in which the x-ray focal spot and the position of the anti-scatter grid are fixed in the direction connecting the x-ray focal spot and the center portion of the surface of the anti-scatter grid (or the sensing surface of the x-ray detector) is employed, also in the case of using x-ray detectors of different spatial resolutions, that is, different sizes in the one direction of the sensing elements for one kind of the anti-scatter grid, the x-ray detector is selected according to the spatial resolution and the position is adjusted by the adjusting means, thereby enabling an image of the subject to be measured.

In the first configuration, the anti-scatter grid (cross anti-scatter grid) is constructed by a first anti-scatter grid in which a first x-ray transmitting member and a first x-ray shielding member are alternately arranged in a first direction, and a second anti-scatter grid in which a second x-ray transmitting member and a second x-ray shielding member are alternately arranged in a second direction which is orthogonal to the first direction, and the first and second anti-scatter grids are disposed so as to be substantially parallel to each other, and integrated so that the center portion of the first anti-scatter grid and the center portion of the second anti-scatter grid substantially coincide with each other.

Further, the pitch in the first direction of the linear projection images on the sensing surface of the x-ray detector of the first x-ray shielding members and the pitch in the second direction of the linear projection images on the sensing surface of the x-ray detector of the second x-ray shielding members are substantially equal to each other. The anti-scatter grid constructed by the first and second scatter grids is a cross anti-scatter grid. Since the structure in which the x-ray shielding members of the anti-scatter grid are arranged two-dimensionally is used, interference of scattering x-rays is little, and a moiré-free image can be obtained with high spatial resolution and high sensitivity.

Further, in the first configuration, the x-ray measuring apparatus further includes means for rotating the x-ray source, the anti-scatter grid, and the x-ray detector in a state where the x-ray source, anti-scatter grid, and x-ray detector are held with fixed relative positions around the subject disposed between the x-ray focal spot and the anti-scatter grid. The data processing means performs data processing of collecting the output signals of the sensing elements at a plurality of rotation angles formed by the rotation and obtaining a sectional image of the subject.

By irradiating the subject with radial x-rays from the x-ray focal spot, cone-beam CT measurement is performed and a moiré-free three-dimensional reconstructed image can be obtained with high spatial resolution and high sensitivity.

In a second configuration of the invention, in a manner similar to the first configuration, a pitch in the first direction of linear images projected on a sensing surface of the x-ray detector of the x-ray shielding members is set to be substantially an integral multiple of two or larger of the pitch of arrangement of the sensing elements in the first direction. By the adjusting means having a function similar to that of the first configuration, the interval is adjusted so that the center of the linear projection image of the x-ray shielding members is positioned substantially in the center of the area of a blind part in the first direction. In a manner similar to the case of the first configuration, also in the case of using a plurality of x-ray detectors of different spatial resolutions for one kind of anti-scatter grid, by selecting an x-ray detector in accordance with a spatial resolution and adjusting the position by the adjusting means, an image of the subject can be measured.

In a third configuration of the invention, a cross anti-scatter grid having the first anti-scatter grid described in the first configuration and a second anti-scatter grid is used as the anti-scatter grid. By adjusting means having a function similar to that of the first configuration, the interval is adjusted so that the center of the linear projection image of the first x-ray shielding member is positioned substantially in the center of the area of the blind part in a first direction, and so that the center of the linear projection image of the second x-ray shielding member is positioned substantially in the center of the area of the blind part in a second direction.

In addition, a pitch in the first direction of linear images projected on the sensing surface of the x-ray detector of the first x-ray shielding members and a pitch in the second direction of linear images projected on a sensing surface of the x-ray detector of the second x-ray shielding members are set to be substantially equal to each other. In a manner similar to the first configuration, an anti-scatter grid (cross anti-scatter grid) having x-ray shielding members arranged two-dimensionally is used, so that interference of scattering x-rays is little and a moiré-free image can be obtained with high spatial resolution and high sensitivity.

The above-described prior art 8 does not disclose an x-ray detector in which the size of a sensing element is smaller than the interval of x-ray shielding members. Although prior art 9 discloses the method of aligning an x-ray source and an anti-scatter grid and prior art 10 discloses a method of aligning an x-ray source and a detector, they do not disclose the method of aligning the anti-scatter grid and the x-ray detector.

BEST MODE FOR CARRYING OUT THE INVENTION

Embodiments of the invention will be described in detail hereinbelow with reference to the diagrams.

Figure 1:
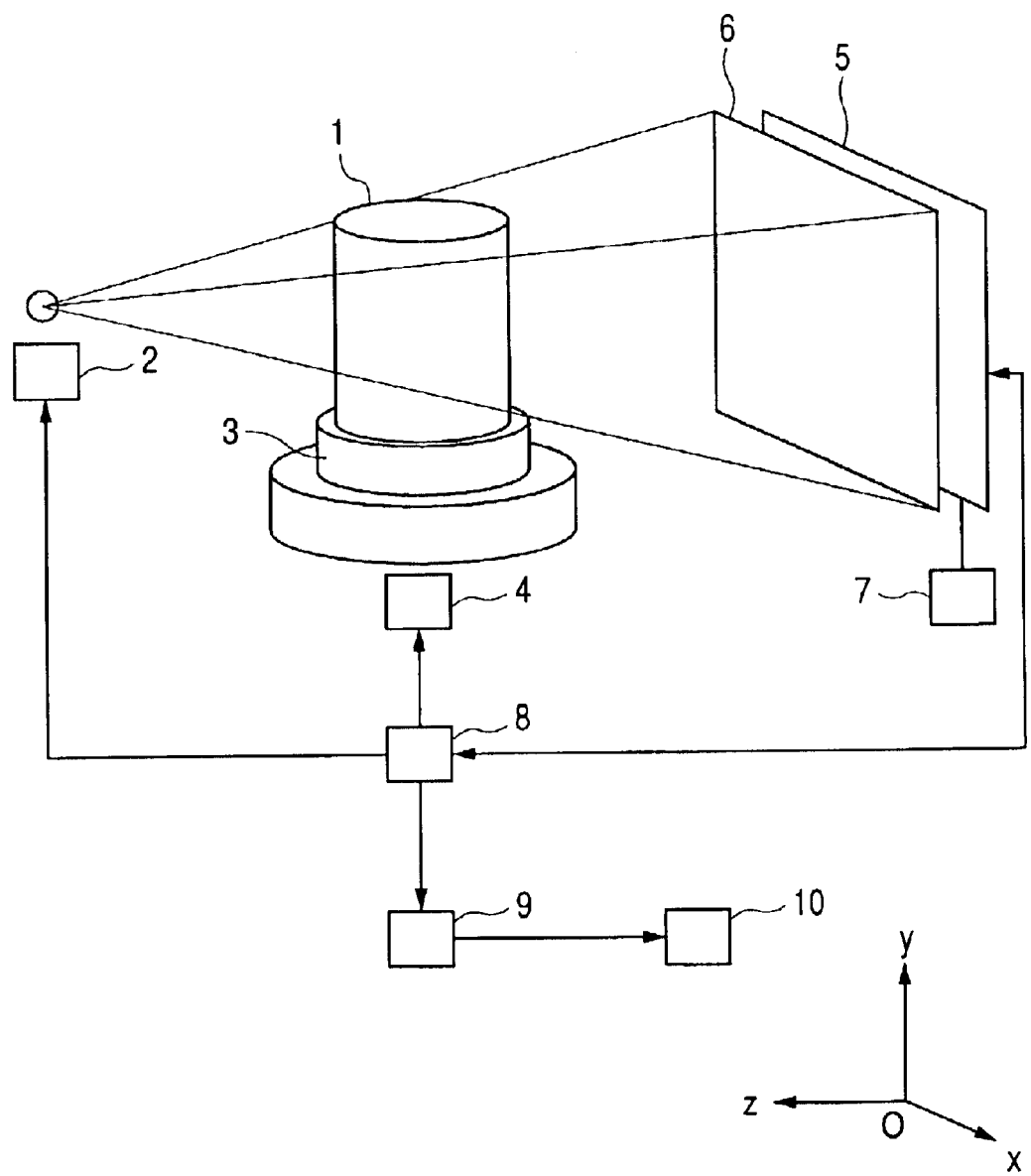
FIG. 1 is a diagram showing an example of the configuration of a cone-beam CT apparatus of an embodiment of the invention.

FIG. 1 is a diagram showing an example of the configuration of a cone-beam CT apparatus of an embodiment of the invention. The cone-beam CT apparatus includes an x-ray tube 2 for emitting x-rays to a subject 1, a table 3 for holding the subject 1, a rotating device 4 for rotating the table 3, an x-ray detector 5 for detecting x-rays passed through the subject 1, an anti-scatter grid 6 for blocking scattering rays, an adjustment device 7 for adjusting the position of the x-ray detector 5 relative to the anti-scatter grid 6, a data acquisition device 8 for acquiring output signals of sensing elements of the x-ray detector 5 by controlling the x-ray tube 2, rotating device 4, and x-ray detector 5, a data processing device 9 for performing a process of computing the acquired data, and a display 10 for displaying the acquired data and the result of the computing process. The data acquisition device 8 can be provided with the function of the data processing device 9.

The set of the anti-scatter grid 6 and the x-ray detector 5 and the x-ray tube 2 are rotated around the subject 1 and cone beam CT measurement is executed. Alternately, it is possible to fix the set of the anti-scatter grid 6 and the x-ray detector 5 and the x-ray tube 2, rotate the subject 1 by the rotating device 4, and perform cone-beam CT measurement.

The x-ray detector is constructed by a plurality of detection units joined to each other. Each of the detection units is constructed by: a fluorescent layer for converting an x-ray incident on each of the detection units into visible light; a converting unit for converting fluorescence generated by the fluorescent layer to an electric signal by an a-SiPD; an amplifying unit for amplifying a signal read from the converting unit by a TFT; a signal output unit for transmitting the signal amplified by the amplifying unit; and a read control unit for controlling reading of a signal in each of the detection units.

The sensing elements in each detection unit, each having a square shape of which one side is 0.127 mm, are arranged at a pitch of 0.127 mm in two directions so as to form a square. A sensitive part of the sensing element has a square shape whose one side is 0.106 mm. The sensitive part is surrounded by a blind part with a width of 0.0105 (=0.021/2) mm. That is, the width of the blind part formed between the sensitive parts of neighboring sensing elements is 0.021 mm.

The x-ray detector is constructed by (3,072×3,072=) 9,437,184 sensing elements arranged at a pitch of 0.127 mm in two direction so as to form a square, and has a square shape whose one side is about 390 mm long.

As the anti-scatter grid, a cross anti-scatter grid obtained by stacking and integrating first and second anti-scatter grids having the same structure is used. Each of the first and second anti-scatter grids uses, as an x-ray shielding member, elongated lead foil having a thickness of 0.050 mm, a height of 1.016 mm, and a length of about 390 mm and uses, as an x-ray transmitting member, elongated aluminum foil having a thickness of about 0.20 mm, a height of 1.016 mm, and a length of about 390 mm.

The anti-scatter grid ratio of the first and second anti-scatter grids is 8:1. The first and second anti-scatter grids are bonded to each other and integrated so that their longitudinal directions of the lead foil perpendicularly cross each other in the center portion of the anti-scatter grids in a state where the center portion of the first anti-scatter grid and that of the second anti-scatter grid coincide with each other and, a face connecting end faces on the x-ray incident side of the lead foil and the aluminum foil of the first anti-scatter grid disposed on the x-ray incident side of the cross anti-scatter grid and a face connecting end faces on the x-ray incident side of the lead foil and the aluminum foil of the second anti-scatter grid disposed on the x-ray outgoing side of the cross anti-scatter grid are held substantially parallel to each other.

That is, the longitudinal direction of the lead foil in the center portion of the first anti-scatter grid is disposed parallel to a first direction, and the longitudinal direction of the lead foil in the center portion of the second anti-scatter grid is disposed parallel to a second direction which perpendicularly crosses the first direction. In such a state, the first and second anti-scatter grids are bonded to each other so as to be integrated.

The distance between the center portion of the plane connecting the end faces on the x-ray incident side of lead foil and aluminum foil of the first anti-scatter grid and the x-ray focal spot is 1.2 m. In the cone-beam CT apparatus of the embodiment of the invention, the interval between the plane connecting the end faces on the x-ray incident side of the lead foil and aluminum foil of the first anti-scatter grid and the sensing surface of the sensing elements of the x-ray detector (surface formed by a plurality of sensitive parts, that is, a plurality of a-SiPDs) is 19 mm.

By moving the sensing surface of the x-ray detector substantially parallel to the plane connecting the end faces on the x-ray incident side in the direction of connecting the center part of the plane connecting the end faces on the x-ray incident side of the first anti-scatter grid and the x-ray focal spot, the position of the sensing surface of the x-ray detector relative to the cross anti-scatter grid is adjusted as follows.

Adjustment is made so that the pitch in the first direction of a linear projection image on the sensing surface of the x-ray detector made of lead foil of the first anti-scatter grid with x-rays becomes substantially twice as large as that of the arrangement of the sensing elements in the first direction, and so that the pitch in the second direction of a linear projection image on the sensing surface of the x-ray detector made of lead foil of the second anti-scatter grid with x-rays becomes substantially twice as large as that of arrangement of the sensing elements in the second direction. Further, the interval between the plane connecting the end faces on the x-ray incident side of the first anti-scatter grid and the sensing surface of the sensing elements of the x-ray detector is adjusted so that the center of the linear projection image of lead foil of the first anti-scatter grid is positioned substantially in the center of the width of the blind part in the first direction, and so that the center of the linear projection image of lead foil of the second anti-scatter grid is positioned substantially in the center of the width of the blind part in the second direction.

Figure 2:
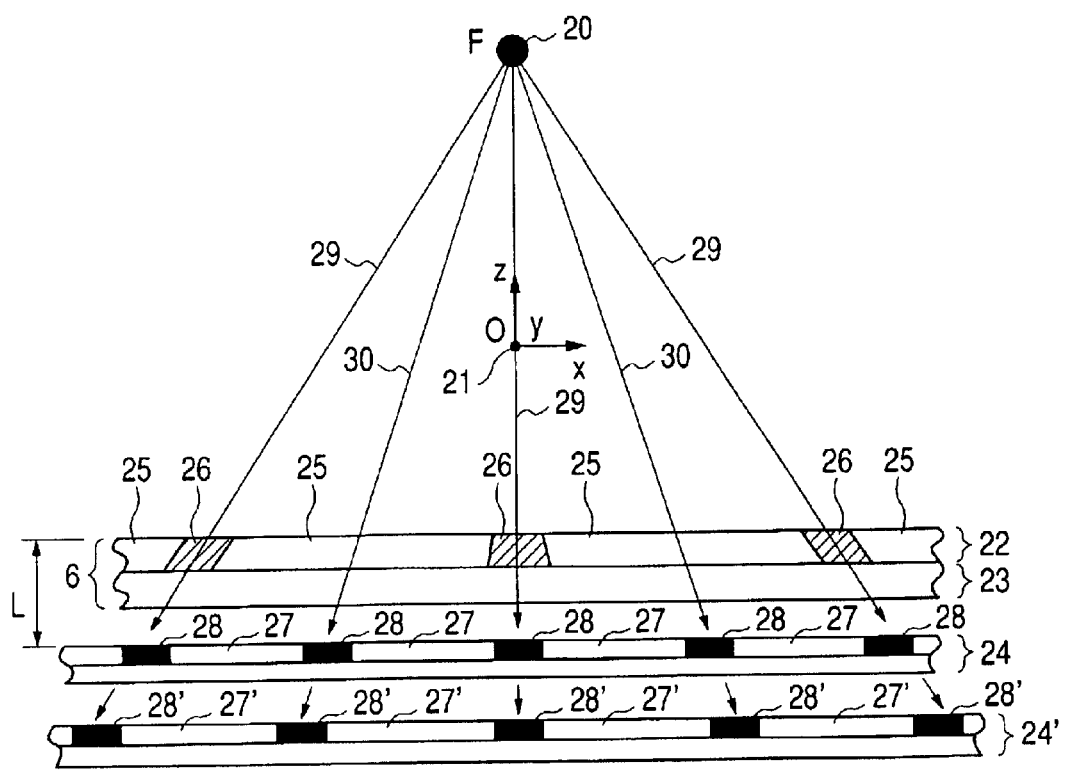
FIG. 2 is a cross section showing an example of the positional relations of lead foil of a cross anti-scatter grid in the cone-beam CT apparatus of the embodiment of the invention and a sensitive part and a blind part of a sensing element in an x-ray detector.

FIG. 2 is a cross section passing through the origin O(21) and parallel to an xz plane, showing an example of the positional relation of the lead foil of the cross anti-scatter grid in the cone-beam CT apparatus in the embodiment of the invention and the sensitive and blind parts of sensing elements of the x-ray detector. The y-axis of a rectangular coordinate system (x, y, z) having the origin O(21) is used as a rotation center axis of the rotating device 4 or a rotation axis of rotating the set of the anti-scatter grid 6 and the x-ray detector 5 and the x-ray tube 2 around the subject 1. An xy plane is set to be parallel to a plane connecting end faces on the x-ray incident side of the first anti-scatter grid 22 of the cross anti-scatter grid 6 constructed by the first and second anti-scatter grids 22 and 23, and a sensing surface (sensitive part) 27 of the sensing elements of the x-ray detector 24. The z-axis is in the direction connecting the focal spot F(20) of an x-ray of the x-ray tube 2 and the center portion of the plane connecting the end faces on the x-ray incident side of the first anti-scatter grid 22.

FIG. 2 shows x-ray paths 29 each passing through the center of lead foil 26 arranged in the x-direction of the first anti-scatter grid 22 and reaching the center in the width of a blind part 28 formed in the x-direction, and x-ray paths 30 each passing through aluminum foil 25 arranged in the x-direction of the first anti-scatter grid 22 and reaching the center in the width of a blind part 28 formed in the x direction. In FIG. 2, the structure of the second anti-scatter grid 23 is not shown.

X-ray detectors 24 and 24' shown in FIG. 2 include the sensing elements having the same size in the x and y directions and the blind parts 28 and 28' having the same width. The spatial resolution of the x-ray detector 24' is lower than that of the x-ray detector 24, and the area of a sensitive part 27' is larger than that of a sensitive part 27 (that is, the size of the sensing element of the x-ray detector 24' is larger than that of the x-ray detector 24).

In FIG. 2, the x-ray detectors 24 and 24' may be shifted from the cross anti-scatter grid 6 in each of the x and y directions only by the half of the size of the sensing element.

Although the example of using the cross anti-scatter grid obtained by integrating the stacked first and second anti-scatter grids having the same structure has been described in FIG. 2, in place of the cross anti-scatter grid shown in FIG. 2, either the first anti-scatter grid in which lead foil is arranged in the x direction or the second anti-scatter grid in which lead foil is arranged in the y direction may be used. In this case as well, it is sufficient to perform relative positioning between the anti-scatter grid and the x-ray detector by the above-described method or a method to be described below.

By moving the sensing surface of the x-ray detector 24 or 24' in a state where it is parallel to the end face on the x-ray incident side of the first anti-scatter grid 22, the position of the sensing surface of the x-ray detector relative to the cross anti-scatter grid is adjusted. In such a manner, a plurality of x-ray detectors having different spatial resolutions can be used for one kind of the first anti-scatter grid 22.

Figure 3:
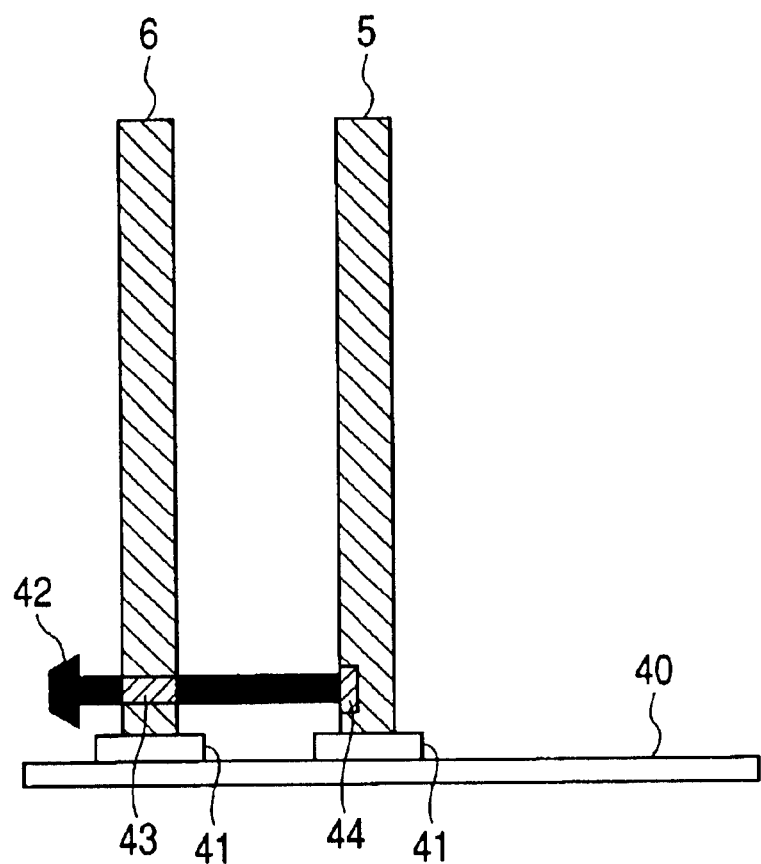
FIG. 3 is a cross section for explaining an example of a method of adjusting the positional relation between the x-ray detector and the anti-scatter grid in the cone-beam CT apparatus of the embodiment of the invention.

FIG. 3 is a cross section for explaining an example of a method of adjusting the positional relation between an x-ray detector and an anti-scatter grid in the cone-beam CT apparatus of the embodiment of the invention. Each of the x-ray detector 5 and the anti-scatter grid 6 is fixed to a sliding plate 41 slidably attached to a frame 40. The x-ray detector 5 and the anti-scatter grid 6 are attached perpendicular to the frame 40.

A screw hole 43 of a screw 42 for adjusting distance is formed in the anti-scatter grid 6, and the screw 42 is screwed in the screw hole 43. The screw 42 is screwed toward the x-ray detector 5. In a part with which the head of the screw 42 comes into contact in the x-ray detector 5, a plate 44 is provided so that the x-ray detector 5 is not damaged by the head of the screw 42. By screwing and pushing the screw 42 to the side of the x-ray detector 5, the distance between the anti-scatter grid 6 and the x-ray detector 5 can be increased in parallel to each other. By screwing the screw 42 so as to be pulled to the side of the anti-scatter grid 6, the distance between the anti-scatter grid 6 and the x-ray detector 5 can be narrowed. Although one screw is used in the example shown in FIG. 3, by further increasing the number of screws, precision of adjustment of the distance can be improved.

The sliding plate 41 to which the anti-scatter grid 6 is fixed is moved so that the center portion of the surface connecting the end faces on the x-ray incident side of the first anti-scatter grid 22 of the anti-scatter grid 6 comes to the position apart from the x-ray focal spot F(20) of the x-ray tube 2 by a predetermined distance, and the sliding plate 41 is fixed to the frame 40. The screw 42 is pushed to the x-ray detector 5 side or pulled to the side of the anti-scatter grid 6. Until the surface of the x-ray detector 5 comes into contact with the head of the screw 42, the sliding plate 41 to which the x-ray detector 5 is fixed is moved. The sliding plate 41 is fixed to the frame 40. In a state where the subject is not disposed, an x-ray is generated to measure an image projected on an x-ray shielding material (lead foil 26) of the x-ray detector 5.

The center position of each of linear projection images on the lead foil in the x and y directions in the projection image, and the center position in the width of the blind part in each of the x and y directions are detected. The sliding plate 41 to which the x-ray detector 5 is fixed is moved to adjust the distance between the anti-scatter grid 6 and the x-ray detector 5 so that the pitch of the center positions of the linear projection images of the lead foil in the x direction substantially becomes twice as large as the pitch of arrangement of the sensing elements in the x direction, the pitch of the center positions of the linear images of the lead foil in the y direction substantially becomes twice as large as the pitch of arrangement of the sensing elements in the y direction, further, the center of the linear projection image of the lead foil in the x direction of the first anti-scatter grid is positioned in the center in the width of the blind part in the x direction, and the center of the linear projection image of the lead foil in the y direction of the second anti-scatter grid is positioned substantially in the center of the width of the blind part in the y direction. Further, whether moiré is seen in the projected image or not is checked. The distance is adjusted until no moiré is seen.

In the cone-beam CT apparatus of the embodiment of the invention, binning of adding output signals of a plurality of sensing elements of the x-ray detector in the x direction and/or the y direction is executed.

In the cone-beam CT apparatus of the embodiment of the invention has two modes of executing the binning. A first binning mode requires longer computation time than the second binning mode but is a high-resolution mode capable of providing an image of high spatial resolution. In the second binning mode, the spatial resolution is lower than an image obtained in the first binning mode but a computing process can be performed at higher speed than the second binning mode. The second mode is a normal mode of normal measuring conditions.

In the high-resolution mode, binning of adding outputs of two sensing elements is performed in each of the x and y directions, thereby adding outputs of total four sensing elements. In the normal mode, binning of adding outputs of four sensing elements in each of the x and y directions is performed, thereby adding outputs of total 16 sensing elements. The ratio between the spatial resolution in the high-resolution mode and the spatial resolution in the normal mode is 1:2.

The number of sensing elements subjected to binning (the number of binning elements), that is, the number of outputs of the sensing elements to be added can be variously changed. At the time of acquiring data, after executing a control of adding outputs of sensing elements, the result of addition is acquired. In such a manner, as the number of elements subjected to binning increases, the faster data can be collected.

It is also possible to employ a configuration in which the number of elements to be bound in the x direction and the number of elements to be bound in the y direction are not equal to each other. For example, the number of elements to be bound in the x direction is not increased while suppressing deterioration in sensitivity, and the number of elements to be bound in the y direction is increased, thereby achieving higher speed and enabling high-sensitive and high-speed data acquisition to be realized.

Figure 4:
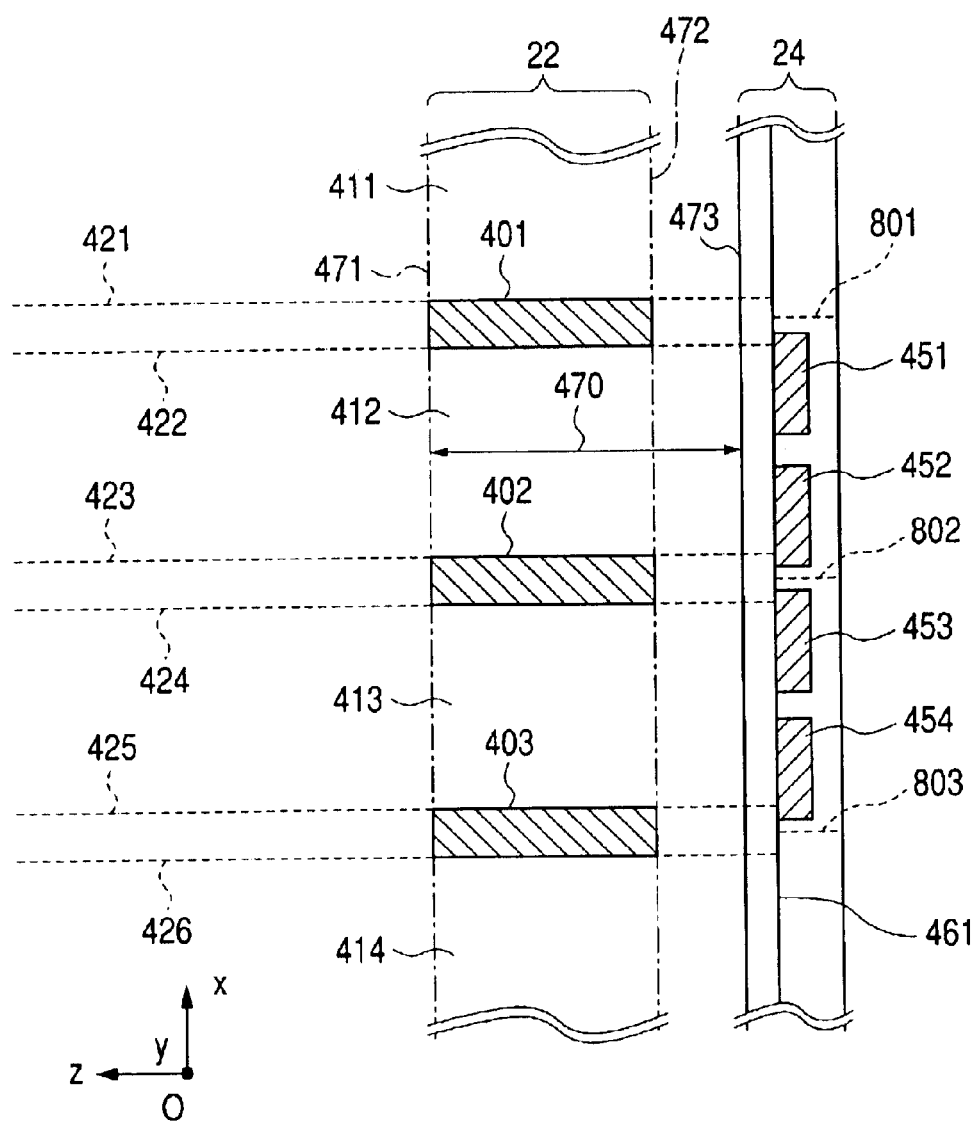
FIG. 4 is an enlarged cross section of a part of x-ray shielding members in the anti-scatter grid and the x-ray detector in the cone-beam CT apparatus of the embodiment of the invention, which is a diagram for explaining the positional relation between the anti-scatter grid and sensing elements.

FIG. 4 is an enlarged cross section which is parallel to the xz plane of a part of the x-ray shielding members of the anti-scatter grid and the x-ray detector in the cone-beam CT apparatus of the embodiment of the invention and which passes the origin O(21). FIG. 4 is a diagram for explaining the positional relation between the anti-scatter grid and the sensing elements.

In FIG. 4, on the left side in the z direction which is not shown in FIG. 4, there is the x-ray focal spot F(20) of the x-ray tube. Dotted lines 421, 422, 423, 424, 425, and 426 indicate paths of x-rays emitted from the x-ray focal spot, propagating along the x-ray shielding member (lead foil) of the anti-scatter grid, and entering the sensing elements. The dotted lines 421 to 426 are not parallel to each other. The paths of x-rays indicated by the dotted lines 421 to 216 are, as exaggerated in FIG. 2, paths of x-ray beams emitted from the x-ray focal spot.

A first anti-scatter grid 22 in the cross anti-scatter grid 6 is constructed by x-ray shielding members (lead foil) 401, 402, and 403 arranged in the x direction and x-ray transmitting members (aluminum foil) 411, 412, 413, and 414 arranged in the x direction. A surface 471 formed by end faces of lead foil and aluminum foil on the x-ray incident side of the first anti-scatter grid 22 and a surface 472 formed by end faces of the lead foil and aluminum foil on the x-ray outgoing side are surfaces which are flush with each other and parallel to the xy plane (the first anti-scatter grid 23 which is not shown in FIG. 4 as well).

In FIG. 4, sensitive parts 451, 452, 453, and 454 of four sensing elements of the x-ray detector 24 are shown. An image of each of the x-ray shielding members and the x-ray transmitting members in the anti-scatter grid is, although slightly, enlarged and projected by x-rays emitted from the x-ray focal spot F(20) onto a sensing surface 461 of the x-ray detector 24. The enlargement ratio is a ratio of the distance between the x-ray focus spot F(20) and the sensing surface 4661 and the distance between the x-ray focus spot F(20) and the surface 471 of the anti-scatter grid. The distance between the surface 471 of the anti-scatter grid and the front face 473 of the x-ray detector is set as L(470).

The positional relation between the position of the anti-scatter grid projected on the sensing surface 461 and the sensitive part in the sensing element will be described hereinbelow. The example shown in FIG. 4 relates to a case where the pitch of images of the x-ray shielding members of the first anti-scatter grid projected on the sensing surface 461 by x-rays from the x-ray focal spot is adjusted to be twice as large as that of formation of the sensing elements.

Dotted lines 801, 802, and 803 show boundary lines of sensing element groups. Outputs of each of the element groups are bound in the high-resolution mode. The position of each of the boundary lines corresponds to the center in the width of a blind part formed between neighboring sensitive parts of the sensing elements.

The binning is executed on four sensing elements of two elements in the x direction and two elements in the y direction in the high-resolution mode. The binning is executed on total 16 sensing elements of four elements in the x direction and four elements in the y direction in the normal mode. That is, in the high-resolution mode, the pitch of images of the x-ray shielding members projected on the sensing surface is the same as that of the group of sensing elements to be subjected to binning. The arrangement pitch of the group of sensing elements subjected to binning in the normal mode is an integral multiple of the arrangement pitch of the group of sensing elements subjected to binning in the high-resolution mode.

Each of the boundary lines 801, 802, and 803 corresponds to the center position in the width of each of the blind parts formed in the x direction. The distance L (470) between the position 471 of the front face of the first anti-scatter grid and the front face 473 of the x-ray detector is changed and adjusted so that each of the boundary lines 801, 802, and 803 coincides with the center position of each of images of the x-ray shielding members arranged in the x direction, which are projected on the sensing surface 471. The distance L (470) is changed by adjusting the position of the front face 473 of the x-ray detector.

As a result, the pitch of images of the x-ray shielding members projected on the sensing surface and the pitch of arrangement of the group of sensing elements subjected to binning coincide with each other, so that occurrence of moiré can be prevented. Since the ratio of shielding the sensitive parts of the sensing elements by the x-ray shielding members can be effectively reduced, sensitivity of the x-ray measuring apparatus is improved. Further, binning in each of the x and y directions is executed on the sensing elements on the inside of the pair of the same x-ray shielding members (for example, in the x direction, a pair of lead foil 401 and the lead foil 402). Therefore, deterioration in the spatial resolution due to addition of outputs of the sensing element group can be suppressed to the minimum.

Figure 5:
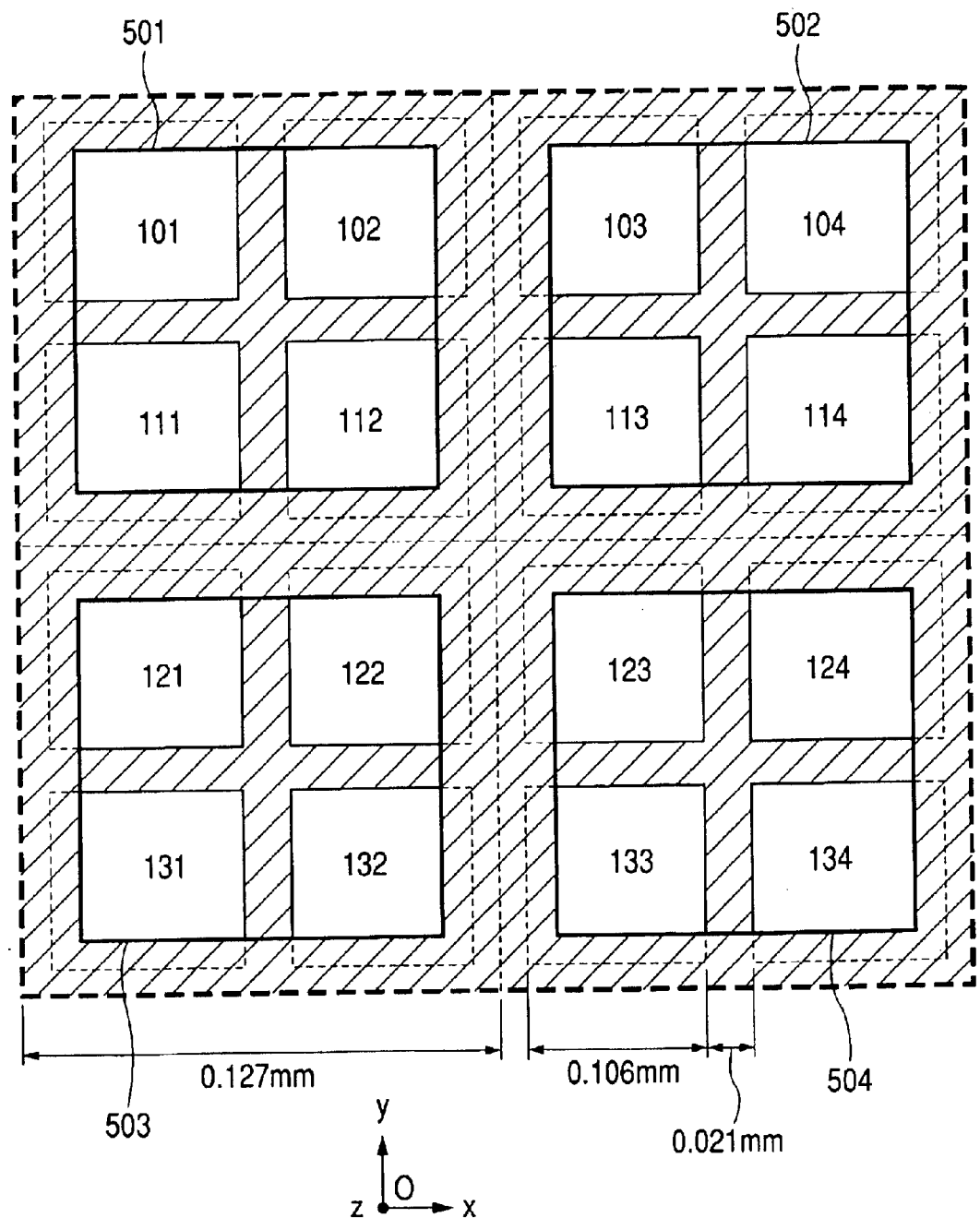
FIG. 5 is a diagram for explaining relative positional relations of x-ray shielding members and a sensitive part and a blind part of a sensing element when the pitch in each of two directions of images projected on a sensing surface of x-ray shielding members arranged in two directions is adjusted to be twice as large as the pitch of sensing elements in the two directions where the sensing elements are formed in the cone-beam CT apparatus of the embodiment, and is a partly enlarged projection in which x-ray shielding members are projected on the sensing surface.
Figure 6:
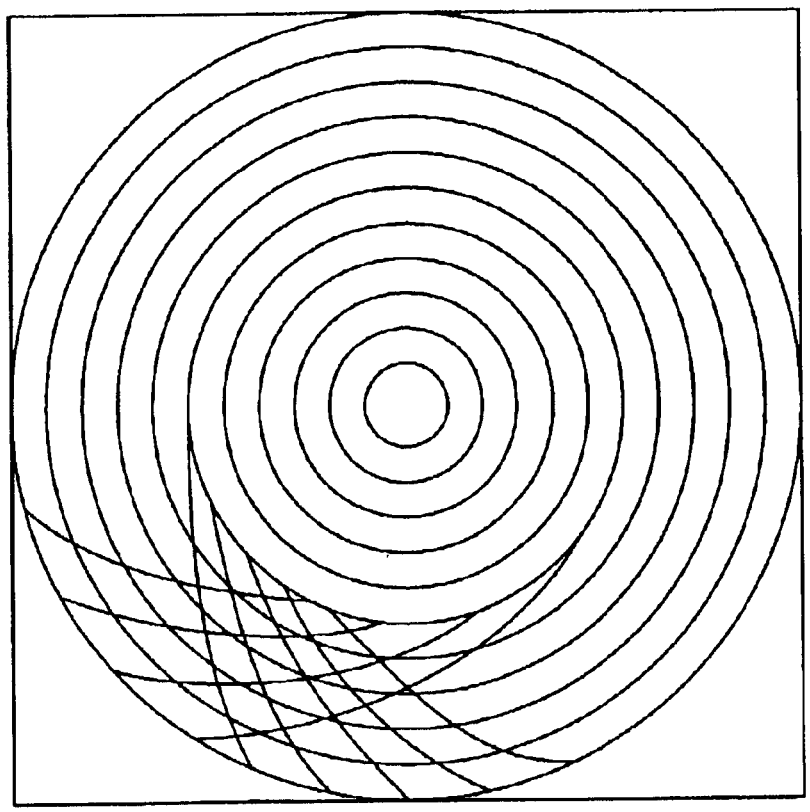
FIG. 6 is a diagram showing an artifact caused by moiré in a conventional cone-beam CT image.

FIG. 5 is a diagram for explaining the relative positional relations of the x-ray shielding members and the sensitive and blind parts of the sensing elements when the pitch in each of the x and y directions in the center position of the images projected on the sensing surface 461 of the x-ray shielding members arranged in the x and y directions is set to be twice as large as that of the sensing elements in each of the x and y directions. FIG. 5 is a partial enlarged projection of the x-ray shielding members projected on the sensing surface 461, which is seen from the direction perpendicular to the drawing sheet of FIG. 4. In the example shown in FIG. 5, in a manner similar to FIGS. 2 and 4, the cross anti-scatter grid constructed by the first and second anti-scatter grids having the same structure is used.

Sensitive parts (each having a size of 0.106 mm×0.106 mm) 101, 102, 103, 104, 111, 112, 113, 114, 121, 122, 123, 124, 131, 132, 133, and 134 of sensing elements (each having a size of 0.127 mm×0.127 mm) formed at equal intervals in the x and y directions are surrounded by the blind parts (having a width of 0.021 mm). The region having a width of 0.015 mm from the periphery of each of the sensitive parts close to two neighboring sides of the sensitive parts is covered with the cross anti-scatter grid (the dimension of the x-ray shielding member projected on the sensing surface 461 is 0.051 mm).

By the x-ray shielding members projected on the sensing surface 461 and by projection of the x-ray shielding members of the cross anti-scatter grid onto the sensing surface 461, holes 501, 502, 503, and 504 by the projection of the x-ray shielding members are formed in the sensing surface 461. In the case of using the cross anti-scatter grid constructed by the first and second anti-scatter grids, the holes 501, 502, 503, 504 are portions in which any of the x-ray shielding members of the first anti-scatter grid and the x-ray shielding members of the second anti-scatter grid are not projected.

The dotted lines shown in FIG. 5 indicate the boundaries of the ranges of the sensing element groups each subjected to binning in the x and y directions. In the example shown in FIG. 5, binning is executed on total four elements of two elements in the x direction and two elements in the y direction.

The position of the sensing surface of the x-ray detector relative to the position of the front face of the first anti-scatter grid in the cross anti-scatter grid is adjusted so that the center of the area occupied by four sensing elements to be subjected to binning and the center of the hole coincide with each other, and the center position in each of the x and y directions of an image projected on the sensing surface of the x-ray shielding members in the cross anti-scatter grid and the center position in the width of the blind part coincide with each other. Specifically, as shown in FIG. 5, the position of the dotted line indicative of the boundary of the range of the sensing element group to be subjected to binning in the x and y directions coincides with the center position of the width of the blind part and the center position in the x and y directions of the image projected on the sensing surface of the x-ray shielding members of the cross anti-scatter grid.

As a result, the pitch of images of the x-ray shielding members of the cross anti-scatter grid projected on the sensing surface and the pitch of arrangement of the sensing element group to be subjected to binning coincide with each other, so that occurrence of moiré can be prevented. Since the ratio of blocking the sensitive parts in the sensing elements with the x-ray shielding members can be effectively reduced, the sensitivity of the x-ray measuring apparatus is improved. Further, the sensing element group to be subjected to binning in the x and y directions is in the hole, and the sensing element group which lies on the inside of the pair of the same x-ray shielding members (for example, in the x direction, the pair of lead foil 401 and 402), so that deterioration in the spatial resolution by addition of outputs of the sensing element group can be suppressed in both of the x and y directions.

In the normal mode, total 16 sensing elements of four sensing elements in the x direction and four sensing elements in the y direction are subjected to binning. As a result, the pitch of images of the x-ray shielding members of the cross anti-scatter grid projected on the sensing surface and the pitch of arrangement of the sensing element group to be subjected to binning coincide with each other, so that occurrence of moiré can be prevented. Since the ratio of blocking the sensitive parts of the sensing elements by the x-ray shielding members can be effectively reduced, the sensitivity of the x-ray measuring apparatus is improved.

Further, binning is executed in the x and y directions on the sensing element group on the inside of the pair of the same x-ray shielding members (for example, in the x direction, the pair of lead foil 401 and 402), so that deterioration in the spatial resolution due to addition of outputs of the sensing element group can be minimized. In the normal mode, by the binning executed on the 16 sensing elements, the spatial resolution deteriorates, but there are effects that the amount of data processing executed after the binning is largely reduced and the computation time is shortened.

In the cone-beam CT apparatus of the embodiment of the invention, binning is executed in two levels. Both of a configuration of executing the binning by hardware before collecting signals from the sensing elements and storing the collected signals into a memory and a configuration of executing the binning by software after the signals are stored in a memory can be employed. The two configurations can be connected in series and used.

The binning on the total four sensitive elements of two sensitive elements in the x direction and two sensitive elements in the y direction is executed by hardware before signals from the sensing elements are stored into a memory. The obtained signal subjected to binning (signal obtained by binning four elements) is collected and stored into a memory. In a post process, binning on four bound signals collected is executed by software.

That is, by combining the pre-process by hardware and the post-process by software, binning on total 16 sensing elements is executed. By using an x-ray detector having the function of hardware capable of executing binning on four sensing elements (four-element binning function), binning on 16 sensitive elements can be executed by software in the post process. As a result, designing of the x-ray detector is generalized and lower cost can be realized. In addition, on the basis of the relation between computation time and spatial resolution, flexibility of the method of using the x-ray measuring apparatus can be increased.

In the case of using the cross anti-scatter grid in which one sensing element corresponds to one hole, there is an effect such that the capability of blocking scattering rays is higher than the case of using a cross anti-scatter grid in which four sensing elements correspond to one hole as shown in the example of FIG. 5. In this case, if the binning is not executed, the center position in the x and y directions of an image projected on the sensing surface of the x-ray shielding members of the anti-scatter grid coincides with the center position in the x and y directions in the width of the blind part in the x and y directions. As a result, the ratio of blocking the sensitive part of a sensing element by the x-ray shielding material can be effectively reduced, so that the sensitivity of the x-ray measuring apparatus is improved. Occurrence of moiré can be also suppressed.

INDUSTRIAL APPLICABILITY

The x-ray measuring apparatus of the invention is applied as an apparatus for diagnosis such as an x-ray image pickup apparatus, an x-ray fluorescent apparatus, or a cone beam CT apparatus capable of acquiring an image of a high picture quality by using an x-ray detector, and produces the following effects.

(1) The ratio of blocking the sensitive part of a sensing element by the x-ray shielding member can be effectively reduced, occurrence of moiré can be prevented, and sensitivity of detecting x-rays can be improved.

(2) Since binning is executed by adding output signals of sensing elements in an area on the inside of a pair of x-ray shielding members, deterioration in spatial resolution by binning can be suppressed to the minimum.

(3) By binning outputs of sensing elements, a moiré-free image can be obtained at high speed with high spatial resolution and high sensitivity.

(4) By adjusting the interval between the anti-scatter grid and the x-ray detector, the same anti-scatter grid can be used for a plurality of x-ray detectors having different pitches of sensing elements. Thus, flexibility of the anti-scatter grid can be increased.

(6) By using a cross anti-scatter grid of which structures in the x and y directions are the same as an anti-scatter grid and the x-ray detector in which the arrangement pitch of sensing elements in the x direction and that in the y direction are the same, the same spatial resolution in both of the x and y directions can be realized.

What is claimed is:

1. An x-ray measuring apparatus comprising:

an x-ray source for emitting x-rays from an x-ray focal spot to a subject;

a flat-type x-ray detector in which a plurality of sensing elements each having a sensitive part and a blind part surrounding the sensitive part are arranged two-dimensionally and which detects an x-ray image which has passed through said subject;

data processing means for collecting output signals of said sensing elements and performing data process on said x-ray image; and an anti-scatter grid which is disposed between said x-ray focal spot and said flat-type x-ray detector, with predetermined distance from the position of said x-ray focal spot and in which an x-ray transmitting member and an x-ray shielding member are alternately arranged in a first direction, wherein a pitch in said first direction of a linear projection image of said x-ray shielding member projected on a sensing surface of said flat-type x-ray detector by said x-ray is set to be substantially an integral multiple of two or larger of the pitch of arrangement of said sensing elements in said first direction, and a center of said linear projection image of said x-ray shielding member is positioned substantially in a center of an area of said blind part in said first direction.

2. The x-ray measuring apparatus according to claim 1, wherein said data processing means performs a process of adding output signals of said plurality of sensing elements which are adjacent to each other.

3. The x-ray measuring apparatus according to claim 1, further comprising:
adjusting means for adjusting an interval between a position of said anti-scatter grid and a position of said flat-type x-ray detector in a direction connecting said x-ray focal spot and a center portion of said anti-scatter grid in a state where the relation between a surface of said anti-scatter grid and said sensing surface of said flat-type x-ray detector is held.

4. The x-ray measuring apparatus according to claim 1, wherein said anti-scatter grid has a first anti-scatter grid in which a first x-ray transmitting member and a first x-ray shielding member are alternately arranged in a first direction, and a second anti-scatter grid in which a second x-ray transmitting member and a second x-ray shielding member are alternately arranged in a second direction which is orthogonal to said first direction, and said first and second anti-scatter grids are disposed so as to be substantially parallel to each other.

5. The x-ray measuring apparatus according to claim 4, wherein a pitch in said first direction of a linear projection image of said first x-ray shielding member projected on said sensing surface and a pitch in said second direction of a linear projection image of said second x-ray shielding member projected on said sensing surface are substantially equal to each other.

6. The x-ray measuring apparatus according to claim 1, further comprising means for giving relative rotation to said subject in a state where relative positions of said x-ray source, said anti-scatter grid, and said flat-type x-ray detector are held around said subject disposed between said x-ray focal spot and said anti-scatter grid,
wherein said data processing means performs data processing of collecting said output signals of said sensing elements at a plurality of rotation angles formed by said rotation and obtaining a sectional image of said subject.

7. The x-ray measuring apparatus according to claim 1, wherein the pitch of said linear projection image of said x-ray shielding member projected on said sensing surface is set to be the same as that of an arrangement of a sensing element group to be subjected to binning.

8. An x-ray measuring apparatus comprising:
an x-ray source for emitting x-rays from an x-ray focal spot to a subject;
a flat-type x-ray detector in which a plurality of sensing elements each having a sensitive part and a blind part surrounding the sensitive part are arranged two-dimensionally and which detects an x-ray image which has passed through said subject;
data processing means for collecting output signals of said sensing elements and performing data processing on said x-ray image;
an anti-scatter grid which is disposed between said x-ray focal spot and said flat-type x-ray detector with a predetermined distance from the position of said x-ray focal spot, and in which an x-ray transmitting member and an x-ray shielding member are alternately arranged in a first direction; and
adjusting means for adjusting an interval between a position of said anti-scatter grid and a position of said flat-type x-ray detector in a direction connecting said x-ray focal spot and a center portion of said anti-scatter grid in a state where the relation between a surface of said anti-scatter grid and a sensing surface of said flat-type x-ray detector is held;
wherein a pitch in said first direction of a linear projection image of said x-ray shielding member projected on said sensing surface is set to be substantially an integral multiple of two or larger of a pitch of an arrangement of said sensing elements in said first direction; and
wherein said interval is adjusted by said adjusting means so that a center of said linear projection image of said x-ray shielding member is positioned substantially in a center of the area of said blind part in said first direction.

9. An x-ray measuring apparatus comprising:
an x-ray source for emitting x-rays from an x-ray focal spot to a subject;
a flat-type x-ray detector in which a plurality of sensing elements each having a sensitive part and a blind part surrounding the sensitive part are arranged two-dimensionally and which detects an x-ray image which has passed through said subject;
data processing means for collecting output signals of said sensing elements and performing data processing on said x-ray image;
an anti-scatter grid having a first anti-scatter grid in which a first x-ray transmitting member and a first x-ray shielding member are alternately arranged in a first direction, and a second anti-scatter grid in which a second x-ray transmitting member and a second x-ray shielding member are alternately arranged in a second direction which is orthogonal to said first direction, said first and second anti-scatter grids being disposed so as to be substantially parallel to each other, and said anti-scatter grid being disposed between said x-ray focal spot and said flat-type x-ray detector, with a predetermined distance from a position of said x-ray focal spot; and
adjusting means for adjusting an interval between a position of said anti-scatter grid and a position of said flat-type x-ray detector in a direction connecting said x-ray focal spot and a center portion of said anti-scatter grid in a state where a surface of said anti-scatter grid and a sensing surface of said flat-type x-ray detector are held to be substantially parallel to each other,
wherein a pitch in said first direction of a linear projection image of said first x-ray shielding member projected on said sensing surface by said x-ray is set to be substantially an integral multiple of two or larger of a pitch of an arrangement of said sensing elements in said first direction, a pitch in said second direction of a linear projection image of said second x-ray shielding member projected on a sensing surface by said x-ray is set to be substantially equal to an integral multiple of two or larger of a pitch of an arrangement of said sensing elements in said second direction, and said interval is adjusted by said adjusting means so that a center of said linear projection image of said first x-ray shielding member is positioned substantially in a center of an area of said blind part in a first direction, and so that a center of said linear projection image of said second x-ray shielding member is positioned substantially in a center of an area of said blind part in a second direction.

10. The x-ray measuring apparatus according to claim 9, wherein the pitch in said first direction of said linear projection image of said first x-ray shielding member projected on said sensing surface and the pitch in said second direction of said linear projection image of said second x-ray shielding member projected on said sensing surface are substantially equal to each other.

* * * * *